United States Patent [19]

Tamari

[11] Patent Number: 5,336,051
[45] Date of Patent: Aug. 9, 1994

[54] INLINE NON-INVASIVE PRESSURE MONITORING SYSTEM FOR PUMPS

[76] Inventor: Yehuda Tamari, 21 Singworth St., Oyster Bay, N.Y. 11771-3703

[21] Appl. No.: 999,215

[22] Filed: Dec. 31, 1992

Related U.S. Application Data

[60] Division of Ser. No. 852,931, Mar. 13, 1992, Pat. No. 5,186,431, which is a continuation of Ser. No. 683,093, Apr. 10, 1991, abandoned, which is a continuation of Ser. No. 410,845, Sep. 22, 1989, abandoned.

[51] Int. Cl.⁵ .............................................. F04B 49/02
[52] U.S. Cl. ..................................... 417/19; 417/474; 604/153
[58] Field of Search ........................ 417/474–479, 417/19, 44; 609/153

[56] References Cited

U.S. PATENT DOCUMENTS

| | | | |
|---|---|---|---|
| 3,062,153 | 11/1962 | Losey | 417/478 |
| 3,105,447 | 10/1963 | Ruppert | 417/477 |
| 3,175,498 | 3/1965 | Rohrer | 417/474 |
| 3,784,323 | 1/1974 | Sausse | 417/477 |
| 4,277,226 | 7/1981 | Archibald | 417/63 |
| 4,515,589 | 5/1985 | Austin et al. | 417/477 |
| 4,563,179 | 1/1986 | Sakai | 607/153 |
| 4,650,471 | 3/1987 | Tamari | 417/474 |
| 4,702,675 | 10/1987 | Aldrovandi et al. | 417/477 |
| 4,836,752 | 6/1989 | Burkett | 417/63 |
| 4,976,593 | 12/1990 | Miyamoto | 417/479 |
| 5,024,347 | 6/1991 | Baldwin | 417/477 |

Primary Examiner—Richard A. Bertsch
Assistant Examiner—Peter Korytnyk
Attorney, Agent, or Firm—Scully, Scott, Murphy & Presser

[57] ABSTRACT

The invention is a pressure sensitive valve that in different forms can be used to provide: an adjustable resistance to flow, adjustable positive or negative pressure relief, negative pressure isolation, isolation of pressure sensitive devices (e.g. pressure monitors) from blood and controlled recirculation between the inlet and outlet of pumps, particularly extracorporeal circulation. The construction of the valve is especially advantageous for extracorporeal circuits, the valve is made from one continuous length of tubing, thereby providing a valve that is more reliable, safer, and has fewer parts. A simple, compact and disposable system to adjust, regulate, and indicate negative or positive pressure applied to the valve is so described.

20 Claims, 7 Drawing Sheets

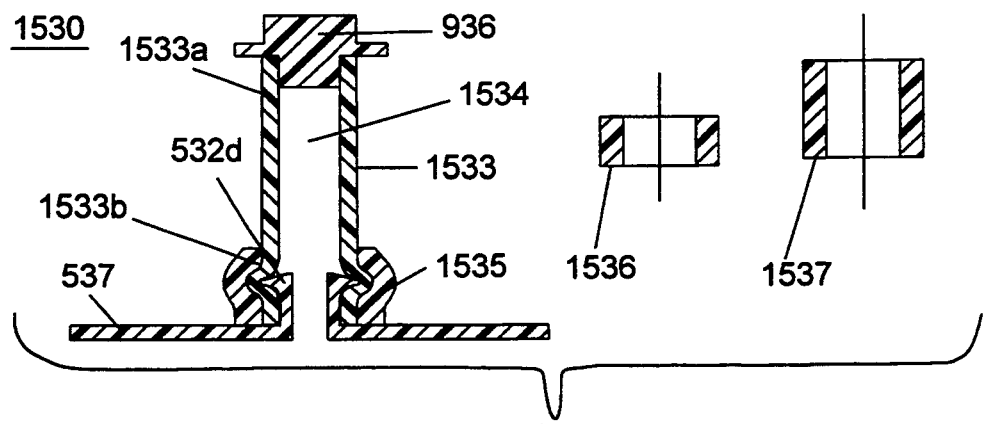
FIG. 15
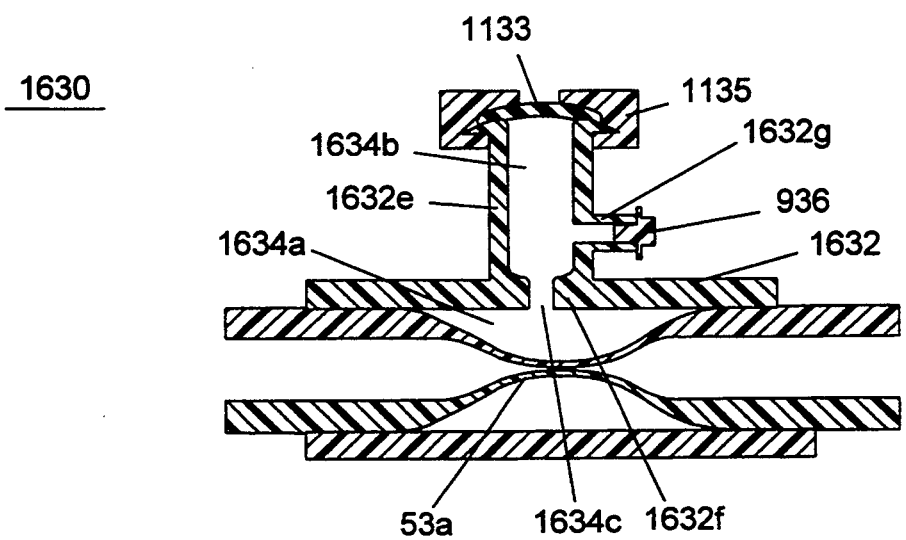
FIG. 16
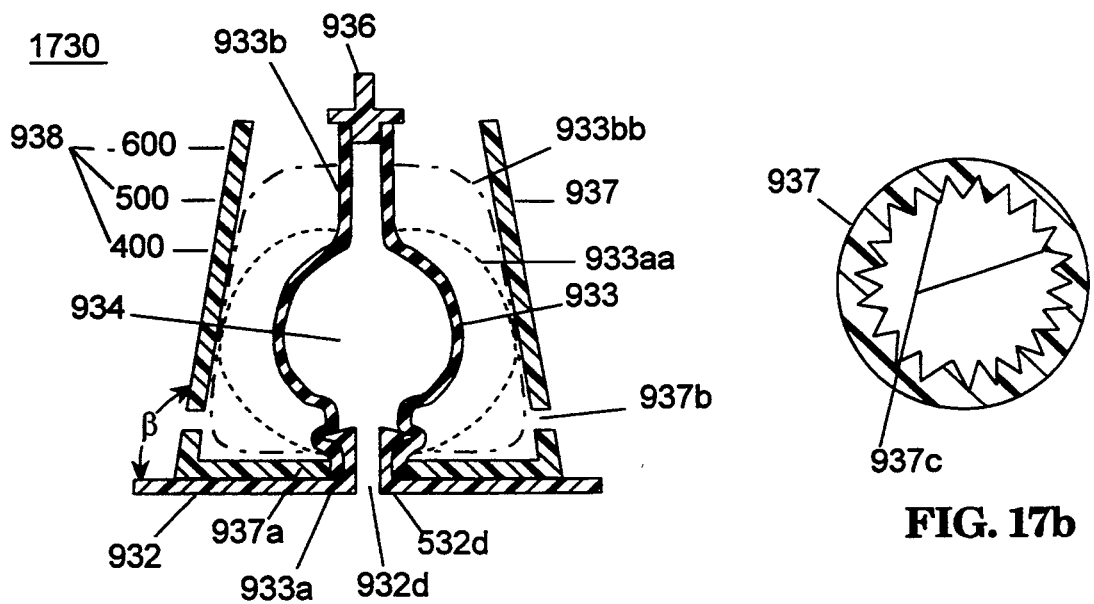
FIG. 17a
FIG. 17b

INLINE NON-INVASIVE PRESSURE MONITORING SYSTEM FOR PUMPS

This application is a division of U.S. Ser. No. 07/852,931 filed Mar. 13, 1992, now U.S. Pat. No. 5,186,431, which was a continuation of U.S. Ser. No. 07/683,093 filed Apr. 10, 1992, now abandoned, which was a continuation of U.S. Ser. No. 07/410,845, filed Sep. 22, 1989, now abandoned, all of which were entitled Pressure Sensitive Values For Extracorporeal Circuits.

CROSS-REFERENCE TO RELATED APPLICATIONS

The application is related to co-pending co-application U.S. Ser. No. 267,235 filed Nov. 3, 1988 now issued, entitled "A Constant Pressure Infusion Device" which contains similar pressure regulators for different applications, the disclosure of said application being incorporated herein by reference thereto.

BACKGROUND OF THE INVENTION

1. Field of the Invention

The invention is a pressure sensitive valve that in different forms can be used to provide: an adjustable resistance to flow, adjustable positive or negative pressure relief, negative pressure isolation, isolation of pressure sensitive devices (e.g. pressure monitors) from blood and controller recirculation between the inlet and outlet or pumps, particularly extracorporeal circulation.

2. Description of the Prior Art

The simplicity and availability of the standard roller pump have made it the choice for extracorporeal circulation. This pump is widely used in dialysis, routine cardiopulmonary bypass and long term pumping such as extracorporeal membrane oxygenators, (ECMO) and left and/or right heart bypass. The standard roller pump maintains a constant flow independent of clinically expected changes in inlet or outlet pressures. Thus, a decrease in blood supply at the pump inlet, without concomitant decrease in pump speed, can cause excessive suction leading to air embolism, thrombosis and damage by the "venous" cannula to the vessel's intima. When a roller pump is used with a bubble oxygenator, a decrease in venous flow that could result in the oxygenator blood level decreasing and in the worst case, air being pumped into the patient. The combination of constant flow and an arterial line that is accidentally clamped or kinked, or an arterial cannula is positioned against the vessel intima, can generate excessive pressures at the outlet of the pump which at the extreme, can blow up a connector, tube or an oxygenator. In addition, the new membranes oxygenerators (the "lung" part of the Heart-Lung machine) are made of microporous membranes that require a positive blood to gas pressure to prevent gas bubbles from entering the blood through the pores. If a negative pressure is applied to the blood side, air can be drawn into the blood stream and pumped to the patient.

To overcome these potential dangers, bubble oxygenators have blood level detectors which stop the pump when the blood level drops below a preset level, or a floating ball valve (as for example made by Health Dyne Cardiovascular Inc. Costa Mesa Calif. 92626) that closes when the blood level drops. In closed systems such as EMCO or dialysis, collapsible bladders have been placed at the inlet to the pump such that at too high a suction, the bladder collapses actuating a microswitch which stops the pump. The pump restarts when the bladder refills. Others have designed roller pump is a servomotor and a microprocessor control system. When the roller pump is used during cardiac surgery for venting the left ventricle or for returning shed blood from the chest cavity it requires constant surveillance by a trained perfusionist to assure that no excess suction is applied. Present solutions to protect against extreme inlet or outlet pressures that may be generated by a roller pump require either on-off control with the standard roller pump, extensive and expensive modifications to the standard pump or a watchful perfusionist. U.S. Pat. Nos. 4,515,589 and 4,767,289 (manufactured by Sarns/3M Corp. as the "Safety Lop"), and 4,650,471, described devices to be used with the roller pump that prevent too much suction. The former provides no adjustment over the pressure about which flow is controlled. The latter has adjustments capabilities for the inlet, but neither one provides relief for overpressurization at the outlet of the pump. Another solution is to use a centrifugal pump such as that made by Biomedicus of Minneapolis Miss. Its flow characteristics permit a limited negative pressure and outlet pressure to be generated, its costs however are high, about $ 10,000 for the pumps module and $ 200 for each of the disposable pump heads.

During CPB it is also necessary to be able to control the venous blood flow to the venous reservoir (e.g. lower flow is required to go on partial bypass). This is usually done by a) raising the venous reservoir relative to the patient, b) partially clamping the venous line either manually with a tubing clamp or c) with a mechanically actuated device the clamps the tubing. Of these method (b) is the most popular because it is simple and does not require additional hardware. However, it is not precise and requires the perfusionist to reach over the venous line that may not always be very accessible.

It is obvious from the above that it would be of great clinical advantage to be able to provide control over the maximum pressure in an extracorporeal circuit and the maximum suction the patient is exposed to, to prevent gas entering the blood stream in a microporous membrane oxygenator, to be able to adjust precisely the resistance to blood flow in a tube as well as provide means that provide the standard roller pump with the advantages of a centrifugal pump without its associated high costs. These can be done with pressure sensitive valves and appropriate control devices.

Prior art pressure sensitive valves are made of the sleeve sealed in a housing with means to pressurize the interluminal space (the space between the housing and the sleeve). Pressure applied to the interluminal space acts upon the wall of the sleeve forcing the opposite wall of the sleeve to meet and close shut. This external force on the wall is counteracted by the pressure within the lumen of the sleeve and the elastic force of the deformed wall which tend to keep the walls apart. It is the net force of these two vectors that determines weather the sleeve is opened, closed or in between.

In industry, these valves are used as ON/OFF valves or as adjustable resistors known as pitch valves. Pinch valves are also used to adjust the resistance to flow using an external roller that pinches and thus controlling the degree of closure of the sleeve. If the wall of the sleeve is made sufficiently thin, the valve can also be used to transfer the pressure of the fluid within the sleeve to the interluminal space without significant changes in the transduced pressure. Thus, these devices can transmit the pressure of a fluid that may be corrosive to a pressure gauge while isolating the pressure gauge from the fluid.

In the medical field such valves, known as Starling resistors, are composed of a thin walled sleeve and required negligible transwall pressure difference to close them. They have been suggested for use to maintain or adjust pressure, (Robert Rushnore: Control of Cardiac Output, in *Physiology and Biophysics* 19$^{th}$ edition Ruch TC and Patton HD editors, WB Saunders Co. Phil. 1965).

U.S. Pat. No. 4,767,289 teaches that a Starling valve may be made of a thin wall tubing, both ends of which are sealed to a rigid connector which in turn are sealed to the housing providing flow through chamber. U.S. Pat. No. 4,515,589 teaches that the walls of the thin wall tubing may extend beyond the housing, be folded upon themselves and sealed over the external wall of the housing. Another manufacturing technique suggests that the inner wall of a resilient sleeve be affixed to the outer wall of the thin walled tubing and the outer wall of that sleeve be affixed to the housing. These techniques have one or more of the following disadvantages: 1) the thin wall tube is stressed over the edges of the housing, 2) the assembly requires sealing the thin wall tube to the connectors, 3) the discontinuities of the valve at the connection sight between the thin wall and the thick wall tubing can create turbulence and trapped vortices, a leading cause of thrombus generation, 4) the assembly is labor intensive and require multiple parts and 5) control over the interluminal pressure with present systems is provided by a cumbersome and bulky combination requiring a compliance chamber, a pressure manometer and interconnecting tubing.

These disadvantages may be the reasons for the lack of pressure sensitive valve available for clinical use. U.S. Pat. No. 4,250,872 by Tamari illustrates a valve made of unitary tubing a portion of which has been expanded and thinned walled to allow easy contraction by external fluid pressure. This valve however was not made to fully close (as illustrated in FIG. 5) nor was it preformed to close completely shut. The only pressure sensitive valve that is known to be used clinically in the extracorporeal circuit is the one incorporated at the inlet to the "Safety Loop" mentioned above. Its assembly is labor intensive and requires multiple parts. In addition, its housing is exposed to atmosphere and provides no mechanism to adjust the interluminal pressure. Senko Medical Instrument Mfg. Co., LTD. of Tokyo Japan manufactures a pressure relief valve intended for dialysis. It is made by interposing a thin wall a diaphragm made of a plastic sheet between the wall with the pressure port and the blood path. This method though very adaptable to mass production, results in a diaphragm that often is accidentally heat-sealed to the housing wall, preventing its free motion, thereby rendering it nonfunctional. It also has discontinuities at the connection sight between the thin wall and the thick wall tubing creating the areas of stagnation which are prone to thrombus formation.

SUMMARY OF THE INVENTION

Briefly, the present invention provides improved pressure sensitive valves and appropriate control mechanisms. The valve is comprised of a thin wall flexible polymeric tubular member sealed in a housing forming an interluminal chamber. The pressure or volume between the thin wall tube and the housing is adjusted via a tube whose one end communicates with the interluminal space and other end connects to means for adjusting negative or positive pressure and/or volume. The thin wall section can be made of a thin wall tube, as described previously, except that the sleeve is affixed directly to the connectors already present in the extracorporeal circuit. The housing is made sufficiently flexible to allow the use of standard tubing clamps to occlude the flow and to expand over the thin wall tube fitted over the rigid connectors so as form mechanical means to affix a sleeve to the rigid connectors. The thin walled portion can also be made from an indefinite single length of thick wall tubing, a portion of which, is processed to provide a the section of thin walled tube required for the valve. The thin wall tubing can have a nominal diameter that is greater than, equal to or smaller than the inside diameter of the thick wall tube. It may also be processed to form different cross sectional areas, which may be more advantageous to control flow through the valve. For example the thin wall tubing can have a flat cross section so, as it closes, it will do so in a venturi patterns to form streamline flow, a more predictable and less traumatic flow pattern, and in addition form a better seal when fully closed (requiring lower pressure differential across the walls of the valve for full closure). Or it may have a circular cross section such that it forms a trisection closure. The interluminal pressure, can for example, be controlled by an elastic balloon whose pressure is essentially unchanged over limited volume changes as described in my co-pending application, U.S. Ser. No. 267,235, referred to above. The interluminal pressure can also be controlled by other mechanisms to be described herein. Either positive or negative pressures can thus be controlled. The objectives of the present invention are to modify, improve and provide a new overall system that can be used to provide adjustable pressure relief valve and a suction shut off valve both of which can be controlled with a simple compact pressure/suction control device.

It is another objective of the present invention to modify, improve and provide a valve to accurately control resistance to blood flow in an extracorporeal circulation.

A further objective of the present invention is to modify, improve and provide a flow through (an inline) isolator between the blood and pressure monitors and/or other devices that require blood pressure (negative or positive) to function and/or control without contaminating the blood.

A further objective of the present invention is to form an extracorporeal circulation regulating valve wherein it replaces standard shunts that are presently clamped, (e.g. arterio-venous or arterial filter shunt). The sleeve of the valve affixed directly to already used "Y-connectors" and sealed within an elastic or flexible housing so as to allow it to be occluded by mechanical clamping, as with a tubing clamp.

A further objective of the present invention is to provide a new overall system that provides the standard roller pump with the advantages of the centrifugal pump with the added advantages of enabling the user to adjust the maximum outlet pressure and minimum inlet pressure, both of which can be controlled with a simple compact pressure/suction control device, and at a significant reduction in cost.

A further objective of the present invention is to make the devices disposable, atraumatic, biocompatible, long lasting, with predictable and clinically useful pressure-flow characteristics.

Other objectives, features and advantages of the present invention will become apparent by reference to the following detailed description of the presently preferred, but nonetheless illustrative, embodiments thereof with reference to the accompanying drawings wherein:

BRIEF DESCRIPTION OF THE DRAWINGS

FIG. 15 is a partial sectional view of another preferred embodiment of the pressure sensitive valves 531 similar to that illustrated in FIG. 14(a) but with a pressure regulator incorporated into the valve housing;

FIG. 16 is a sectional view of a simple pressure regulating embodiment to be used with pressure sensitive valves 531 similar to that illustrated in FIG. 14(a) but with a pressure regulator incorporated into the valve housing that provides adjustable pressure control;

FIG. 17(a) is a sectional view of a preferred embodiment of an adjustable pressure regulator to be used with pressure sensitive valve as illustrated in FIG. 14(a);

FIG. 17(b) is a cross sectional view illustrating a preferred topography of the internal wall of the regulator's housing illustrated in FIG. 17(a);

DETAILED DESCRIPTION OF THE PREFERRED EMBODIMENTS

Figure 1:
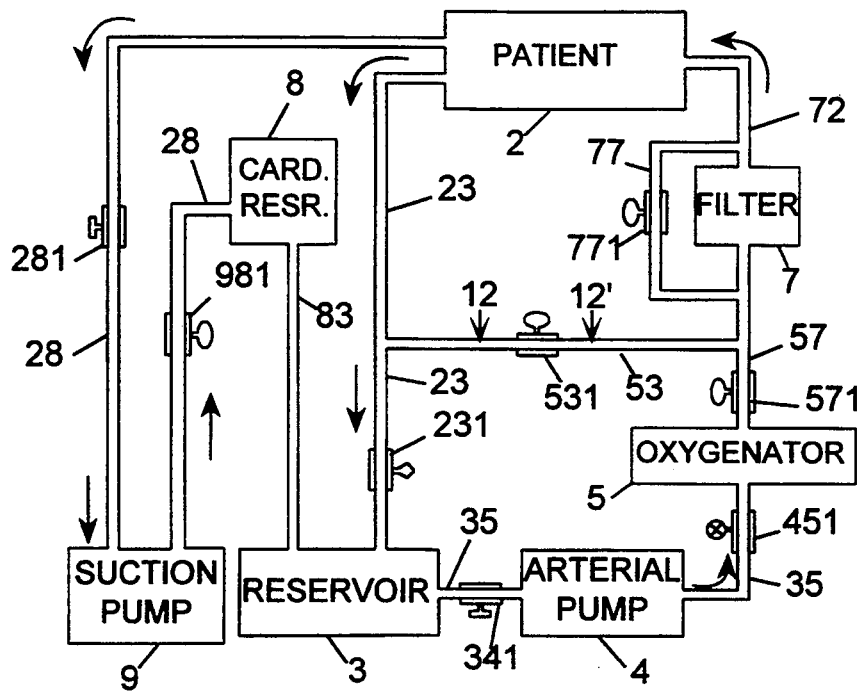
FIG. 1 is a schematic representation of a system according to the present invention and showing particularly pressure sensitive valves in various locations of a clinical cardiopulmonary bypass circuit, each valve with an associated pressure control device for controlling the valve according to its respective function.

Reference should now be made to the drawings wherein the same reference numerals are used throughout to designate the same or similar parts.

A typical extracorporeal circuit to which pressure sensitive valves in accordance with the present invention may be applied is illustrated in FIG. 1 as including a section of tubing 23 inserted at one end by means of a cannula (not shown) in the vena cavae for obtaining venous blood from the heart (not shown) of patient 2. Tubing 23 is coupled, as an example, to a venous reservoir 3 from which the blood is drawn via tube 35 by roller pump 4 and pumped through a membrane oxygenator 5 wherein oxygen is supplied to the blood and carbon dioxide removed. The blood from the oxygenator is then conducted by means of tubing 57 to arterial filter 7 and then via tubing 72 and an arterial cannula (not shown) back to the patient. Blood spilling into the chest cavity (not shown) is collected via unitary tubing 28 by suction generated by roller pump 9 and pumped into cardiotomy reservoir 8 from which it flows by gravity drainage through unitary tubing 83 into venous reservoir 3.

A volume sensitive valve 231 is inserted between the patient and the inlet to venous reservoir 3 in unitary tubing 23. As will be hereinafter explained in detail, by adjusting the interluminal volume or pressure of valve 231, it is possible to vary the resistance to flow thereby controlling the venous blood flow to the venous reservoir. The interluminal volume can be adjusted by adding or removing volume with compressible or incompressible fluid. The use of incompressible fluid provides more accurate control over the absolute opening of the valve. Utilizing a sterile physiological solutions, as for example saline, as the incompressible solution also provides a safety feature: should the thin wall section develop a leak, the blood would not be contaminated nor would it be exposed to a gas that could cause gas embolus.

A pressure sensitive valve 341 is inserted between the reservoir and the inlet to roller pump 4 in unitary tubing 35, which protects against pumping air to the patient should the reservoir empty. As will be hereinafter explained in detail, this is achieved by having the valve collapse to a closed state when the blood pressure decreases below a preset value usually equal to hydraulic pressure exerted by the minimum acceptable blood level of venous reservoir 3. Valve 341 reopens when the blood pressure reaches a value greater then the preset value of the valve. It should be noted that a volume sensitive valve is similar to a pressure sensitive valve except that the wall of the former may be thicker.

In the circuit shown in FIG. 1, it is necessary to prevent the entry of air into the blood stream through the micropores of a membrane oxygenator 5 if the gas pressure is greater than the blood pressure. This can occur when the membrane oxygenator is above the venous reservoir 3 or the gas outlet port is obstructed. To prevent the former, presently the venous reservoir 3 must be positioned above the membrane oxygenator, thus limiting venous drainage. An additional 20 to 30% increase in venous drainage could be provided if the reservoir could be placed below the membrane oxygenator. This can be achieved by placing a prepressurized pressure relief valve at the inlet and outlet of the membrane oxygenator: combination isolator and pressure sensitive valve 451 as described hereinafter, is inserted in unitary tubing 35 between pump 4 and the inlet to oxygenator 5, and pressure sensitive valve 571 is inserted into unitary tubing 57 at the outlet of oxygenator 5. The valves open when the inlet blood pressure is greater than the hydraulic height between the reservoir and the oxygenator. Thus, the two valves isolate the microporous oxygenator from the venous reservoir and assure that the pressure on the blood side of the microporous oxygenator is always above atmospheric pressure on the gas side. This has the advantage of being able to place the venous reservoir below the membrane oxygenator thereby providing greater gravity drainage presently not possible with microporous membrane oxygenator. The pressure isolator of combination valve 451 also provides means to measure arterial line pressure without direct blood contact.

A pressure sensitive valve 531, acting as a pressure relief valve, inserted into unitary tubing 53 between the inlet and outlet of arterial pump 4, shown connected at oxygenator outlet tube 57 and venous line 23, prevents accidental overpressurization at the outlet of pump 4. The use of this valve provides additional clinical advantages not possible with the standard roller pump. For example, at the end of the operation when the patient is off cardiopulmonary bypass (CPB), blood is administrated to the patient by pumping from the oxygenator through the arterial cannula. The surgeon tells the perfusionist to infuse 100 ml, the perfusionist unclamps the arterial line, turns the pump till 100 ml are infused and then shuts the pump off and reclamps the arterial line. This procedure requires coordination and the is dependent on the perfusionist. With pressure relief valve 531 as the shunt between the arterial and venous line, the roller pump can be left on continuously and the surgeon can control blood administration directly by opening and closing the tubing clamp himself. Another advantage is that the bypass line 77 used across the inlet and outlet of the arterial filter (see below) may not be necessary. Should the filter plug up, valve 531 would open to prevent over pressurization of the arterial line and in addition would divert the blood from the patient back to the venous line. This is especially useful should the build up in pressure be due to thrombus. It should be noted that should valve 531 open during CPB the blood volume at the inlet to the pump will tend to increase. This increase would be unlimited with an "open system" (e.g. bubble oxygenator) but would be limited to the capacity of the inlet reservoir (e.g. venous reservoir of membrane oxygenator). This implies that the use of a recirculating valve will benefit from an indicator that the valve is open. Reduction in flow to the patient can be indicated by reduction in the arterial pressure of the patient, a flow meter attached to the arterial line between valve 531 and the patient, or an alarm to indicate whenever the valve opens, as described hereinafter.

A pressure relief valve, 771, can also be inserted across the inlet and outlet of the arterial filter in unitary tubing 77, to prevent over pressurization of the arterial line due to a plugged filter.

A suction control valve 281 is inserted between the patient chest cavity (not shown) or a vented heart chamber (not shown) and the inlet to suction pump 9, and protects the patient 2 from excess negative pressure. This valve stays open as long as the blood pressure between the pump and the patient is higher than that set by the user or manufacturer.

A pressure sensitive valve 981 may be inserted into unitary tubing 28, between roller pump 9 and the inlet to cardiotomy reservoir 8, and opens only if the blood pressure is above the interluminal pressure. If the interluminal pressure is maintained slightly positive, and the cardiotomy reservoir 8 is open to atmosphere, then if suction pump 9, when used for venting one of the heart chambers, is accidentally reversed, valve 981 would close, preventing pumping air back to the patient.

As described, a pressure sensitive valve can be used to: open and relieve excess pressure, close when the pressure drops too low, adjust resistance to flow and transmit a pressure signal across its wall. Each application may require a slightly different design. The specific operation, related design and different applications of each valve is hereinafter described.

Figure 2:
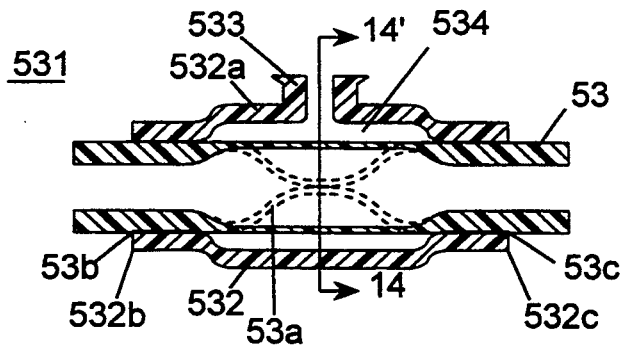
FIG. 2 is a sectional view of valve 531 taken between lines 12 and 12' in FIG. 1 illustrating one preferred embodiment of a pressure sensitive valve.
Figure 3:
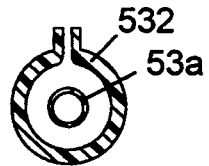
FIG. 3 is a transverse sectional view taken along lines 14 and 14' in FIG. 2 showing the expanded configuration of the inner thin wall tubing.

FIG. 2 illustrates one presently preferred embodiment of the pressure sensitive valve which is illustrated in use in FIG. 1 as 231, 281, 341, 531, 571, 771, and 981. Valve 531 includes a unitary tubing member 53 passing through a generally cylindrical or elliptical housing or enclosure 532 which is nonelastic in construction using thermoplastic material such as clear polycarbonate, polyvinylchloride, polyethylene or the like. Tubing member 53 preferably consists of a continuous length of blood compatible flexible polymeric material having a smooth fissureless inner surface throughout. It is useful for the material to be thermoplastic so as to allow the formation of the thin wall after the tube has been extruded. It may be formed from polyvinylchloride, polyurethane or the like. As illustrated, it has a region 53a intermediate its ends which region has an inside diameter greater than the inside diameter of the remainder of the tube and a thinner wall than that of the remainder of the tube. The tubing has a gradual transition in wall thickness between the two inside diameters. The rigid walled enclosure 532 surrounds region 53a and seals it about regions 53b and 53c of said tubing. Inlet opening 532b and outlet opening 532c of housing 532 are snug fit to seal to the outside normal diameter of tubing member 53 on either side beyond the central region 53a. The midportion of housing 532 has an enlarged region 532a, which accommodates the region 53a of unitary tubing 53. A duct 533 is joined to (or formed at) housing 532 and communicates with chamber 534, formed between the housing 532 and region 53a. Duct 533 is then connected to a pressure controller such as the pressure controller illustrated in FIG. 9. For the purpose of sealing seals 52b and 52c via radio frequency, heat sealing or adhesive, or for other connective purposes it is advantageous to form the housing 532 of the same material as the unitary tubing 53. Housing 532 may also be designed to serve as mechanical support for the thin section of region 53a to prevent accidental rupture due to over-herniation of region 53a which could occur when the interluminal pressure is low and the blood pressure is high.

Figure 4:
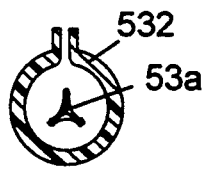
FIG. 4 is a transverse sectional view of pressure sensitive valve similar to that of FIG. 3 but with the tubing member illustrated contracted in a triangular closure.
Figure 5:
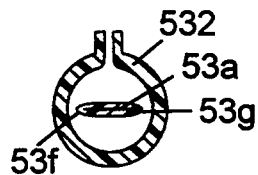
FIG. 5 is a transverse sectional view of pressure sensitive valve of FIG. 2 similar to that of FIG. 4 but with the tubing member illustrated contracted in a flat closure.
Figure 6:
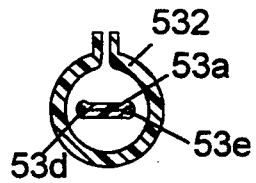
FIG. 6 is a transverse sectional view of pressure sensitive valve in a contracted state similar to that of FIG. 5 but modified to form two channels.

During the operation of the pressure sensitive valve, pressurized fluid (or fluid mass) is introduced through duct 533 into chamber 534 whereupon the pressure causes indentation or contraction of the thin walled region 53a of the tubing to displace any blood contained therein leading to controlled restriction of the blood flow in unitary tubing 53, from the arterial line 57 to venous line 23. This restriction can be complete as illustrated in FIG. 5 or with small channels 53d and 53e that provide a low leak, illustrated by FIG. 6 and described hereinafter. To assure full closure of section 53a as illustrated in FIG. 5 at lower pressure differences between controlling interluminal pressure and blood pressure, edges 53g and 53f are preformed, for example with heat, to overcome the otherwise relatively high stresses inherent in the material that resist folding. It should be understood that for valves used to isolate (e.g. valve 571 isolating oxygenator 5 in FIG. 1) a complete obstruction to flow, as illustrated in FIG. 4, and 5, is required and the channels illustrated at 53a in FIG. 6 are undesirable.

As long as the fluid pressure in chamber 534 acting externally on the thin wall tube is greater than the pressure inside the tubing, the valve remains closed. If the pressure inside the tubing is greater than the external fluid pressure, the valve opens. If the pressure at the inlet to the valve is higher and the pressure at the outlet is lower than external pressure then the valve does open, but only partially, and serves as a resistor that maintains inlet pressure at a pressure approximately equal to the fluid pressure applied in chamber 534. It should be understood that when the valve is used at the outlet of a constant flow roller pump, the cross sectional area opened to flow decreases as the thin walled region of the valve collapses. The combination of decreased area and constant flow, causes blood velocity and the blood pressure in region 53a to increase and decrease respectively according to Berniulli's equation. The lower blood pressure in region 53a reduces the gas pressure at which the valve will close. If the resistance at the outlet is low, as is the case between valve 531 outlet and venous reservoir 3, then the valve will flutter between open and closed positions, the oscillation frequency being higher with low viscosity (dilute blood) and high Reynold's numbers (higher flow rates). This property can be used to alarm the user to an open valve condition. For example, if the pressure sensitive valve is used as a pressure relief valve between the arterial and venous lines (531) or across the inlet and outlet of an arterial filter (771), then clinically it would be very useful to have an alarm incorporated into the valve design to alert the user of a dangerous condition. This can be done with the fluttering that occurs when the valve opens. For other uses, as for example the pressure sensitive valve acting as a resistor (231), or a continuous recirculating line, it is undesirable to have fluttering because over time it may cause blood damage. It therefore would be very useful to be able to control the degree of or eliminate fluttering. Such a method has been invented.

Figure 9:
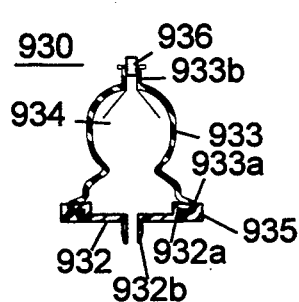
FIG. 9 is a sectional view of one preferred embodiment of a pressure regulator for the pressure sensitive valve utilizing a spherical elastic balloon.
Figure 10:
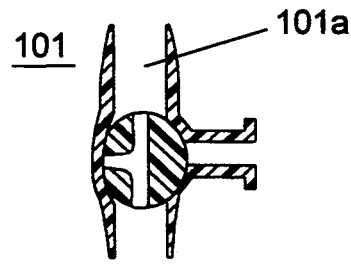
FIG. 10 is a sectional view of a valve used to control resistance to fluid flow between pressure regulator and pressure relief valve.

The method consists of using an adjustable valve 101 as illustrated in FIG. 10 between the interluminal space 534 of valve 531 and the pressure regulator 930 illustrated in FIG. 9. This valve, in combination with the choice of a fluid of appropriate viscosity in interluminal space 534, conduit 101a and chamber 934, can be used to control the rate of volume change between the interluminal space and the pressure regulator and thus the rate at which valve 531 can open or close. Increasing the resistance by closing valve 101 (or by increasing the viscosity of the fluid) reduces the flow rate between chamber 534 and the pressure regulator 930 thus providing decreased damping. The resistance can also be controlled by inserting various lengths and/or diameters of tubing between chamber 534 and pressure regulator 930. Another method that may reduce fluttering is to increase the diameter of region 53a (illustrated in FIG. 2 and FIG. 14(a)) so as to decrease the velocity of the blood therethrough and thereby reduce the pressure differences across the wall of region 53a that is due to differences in blood velocity in region 53a and the normal section of unitary tubing 53. Alternately, an equal or smaller ID in region 53a (illustrated in FIG. 7 as 53a) may increase the chance of flutter, a flow characteristic desirable for the aforementioned alarm.

Another method to alarm the user to an open valve is to channel the pressure signal from port 533 to an arterial line pressure monitor with an alarm system (as made by DLP of Grand Rapids Mich.). Increased blood pressure would force the valve open reducing interluminal space 534, thereby transmitting the increased pressure to the pressure monitor. Pressure transmission would be best achieved with a mixture of gas and liquid in Chamber 534. The ratio of liquid to gas can be adjusted to provide sufficient compliance for the valve to open without causing an undue increase in control pressure but with sufficient pressure increase for the pressure monitor to sense the increase.

If the walls of region 53a of unitary tubing 53 are made sufficiently thin and with insignificant memory, valve 531 can be used to transfer the pressure of the fluid within unitary tubing 53 to the interluminal space 534 from which a pressure may be derived, for example to an electronic pressure transducer (not shown). The volume change in chamber 534 that can accommodate pressure transfer equals the volume change due to that volume change caused by the walls of region 53a as they move from a collapsed state to an expanded state, the collapsed state starting from, and the expanded state ending with, the walls of region 53a freely moving, without significant stresses in the walls, to interfere with the required accuracy and fidelity of the pressure signal. The pressure sensitive valve can therefore replace devices such as PMS-3 Pressure Monitor Separator made by Healthdyne Cardiovascular Inc. Costa Mesa Calif. 92626, that are attached to prior art "T-connectors" in the line. Replacing a "T-connector" with the pressure sensitive valve, which is an inline device, has the advantage of eliminating stasis conditions which can promote thrombus formation. The fluid used to transmit the pressure from the interluminal space to a pressure transducer can be a liquid such as normal saline or gas such as air.

Figure 25:
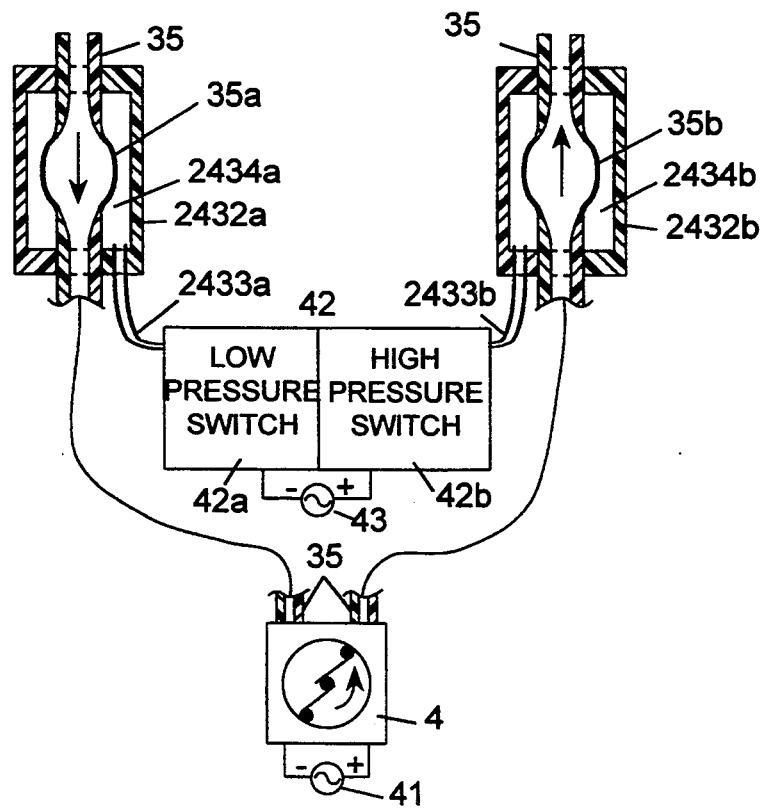
FIG. 25 illustrates one of many setups utilizing pressure sensitive valves to control excess negative and positive pressures at the inlet and outlet of the standard roller pump respectively.

The pressure signal from pressure isolator valve 53 can also be used to turn the roller pump on and off. For example, the pressure signal can be connected to an electromechanical pressure switch (e.g. Model #MPL 533 of MPL Fort Lauderdale Fla.) set by the user, such that whenever the set pressure is reached, the electrical power to the roller pump shuts off. For example, the device can be interposed between roller pump 4 and the standard electrical wall outlet (not shown), power cord 41 of the pump is plugged into the device and the device, through plug 43, plugs into the wall, see FIG. 25. The device incorporates pressure sensitive electrical switch 42b that is normally closed, but opens when the pressure it monitors reaches a preset level. Thus, the pressure from the pressure isolator incorporating housing 2432b is connected via conduit 2433b to pressure switch 42b, electrical plug 41 of the roller pump is plugged into device 42, and device 42 is plugged into the standard wall outlet. As long as the blood pressure within tube 35b is below the preset pressure in interluminal chamber 2434b, the switch is closed and the pump is electrically powered. If the pressure in tube 35b exceeds the actuating pressure of pressure sensitive switch 42b, the switch opens the electrical circuit shutting off the power to pump 4.

The device can incorporate a second pressure sensitive electrical switch 42a that is normally closed, but opens when the pressure at the inlet to pump 4 falls below a preset value. Thus, the pressure from the pressure isolator incorporating housing 2432a is connected via conduit 2433a to pressure switch 42a. As long as the blood pressure within tube 35a is above the preset pressure in interluminal chamber 2434a, the switch is closed and the pump is electrically powered. If the pressure in tube 35a falls below the preset pressure of pressure sensitive switch 42a, the switch opens the electrical circuit, shutting off the power to pump 4. Thus, device 42 in combination with two pressure isolation valves can prevent excess inlet and/or outlet pressure that may be generated by pump 4. Note that the two valves and the pumping segment therebetween are all made of one continuous length of tubing.

FIG. 6 illustrates housing 532 and tubing member 53a therein in a state of contraction with a two-way closure, with opposite walls flattened out to make contact and form a closure with two channels at the edges 53d and 53e. These channels allow sufficient blood flow through the tubing to hinder clot formation in tube 53 and valve 531 without taking away from its main purpose of causing a main obstruction to flow. The channels may be formed naturally by the elastic properties of the material which dictate that the greatest stresses occur along the edges that fold. Or if necessary, the channels may also be formed by heating the thin walled section and forming the channels with appropriate dies. The low flow provided by the leak can prevent stagnation of blood and thus prevent thrombus formation. To further reduce the occurrence of thrombus, it is advantageous to increase the blood velocity in tube 53. This can be achieved by making the diameter of unitary tube 53 smaller than the diameter used for the arterial, 57, or venous, 23, tubing. The diameter of 53 could be equivalent to the diameter of the arterial cannula. For valves 531 and 771 this may be for example 5 to 10% of the flow in tubing 57. Though two channels are shown, it should be understood that a similar function can be served by one or more channels.

Figure 7:
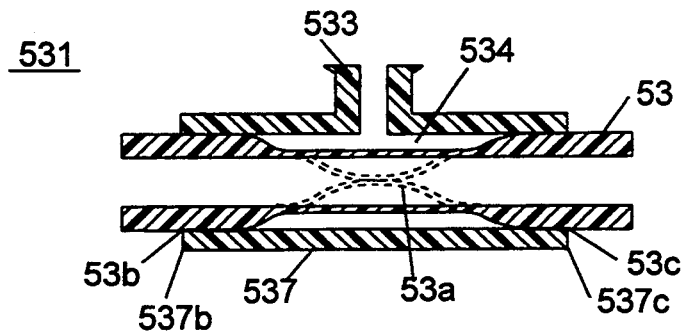
FIG. 7 is a longitudinal sectional view of pressure sensitive valve similar to that of FIG. 2 but showing a modification of the device.

Referring to FIG. 7, another preferred embodiment of the present invention similar to that of FIG. 2 is illustrated with a modification of region 53a intermediate its ends whereby region has an inside diameter equal to or smaller than the inside diameter of the remainder of unitary tubing 53 and a thinner wall than that of the remainder of said tubing with a gradual transition in wall thickness between the outside diameters thereof. The rigid walled enclosure 537, has an inside diameter made to snugly fit the outside diameter of unitary tubing 53, and surrounds and seals region 53a within said enclosure. Inlet opening 537b and outlet opening 537c of housing 532 are sealed to 53b and 53c of the outside normal diameter of tubing member 53 on either side beyond the central region 53a. Duct 533 is joined or formed to the portion of housing 537 which overlays region 53a of tube 53. Duct 533 provides a means for interconnecting the interluminal space 534 formed between housing 537 and region 53a to the pressure controller outlet fitting 932b illustrated in FIG. 9.

Alternatively, unitary tubing 53 can be formed of a highly elastic material such as silicone rubber, in which section 53a is permanently formed in the closed position as illustrated in FIG. 5, or FIG. 6, said section then requiring a precalculated blood pressure above the pressure in the interluminal space 534 to open section 53a of pressure sensitive valve 531. The precalculated pressure can be fixed during manufacturing by adjusting the thickness of section 53a and the degree of stress put on the material. It should be understood that when valve 531 is made with an elastic section 53a then the wall thickness of section 53a can be thicker than the normal wall of unitary tubing 53. It also should be understood that unitary tubing 53 need not be made the entire length of tubing 57 and 23 illustrated in FIG. 1, but can be made to connect in the standard manner as is known to those practicing in the art.

Another alternate embodiment is to form the cylindrical housing 537 of an elastic material, wherein ends 537b and 537c are sealed to 53b and 53c of unitary tube 53 respectively. The seal can be mechanical, with adhesive, or with an intermediate sleeve as illustrated by sleeves 2353 and 2354 in FIG. 23 between the tubing and the walls of housing 537. Housing 537 may be formed with walls having the elastic properties that will be hereinafter described with respect to FIG. 9 and FIG. 15.

Figure 14A:
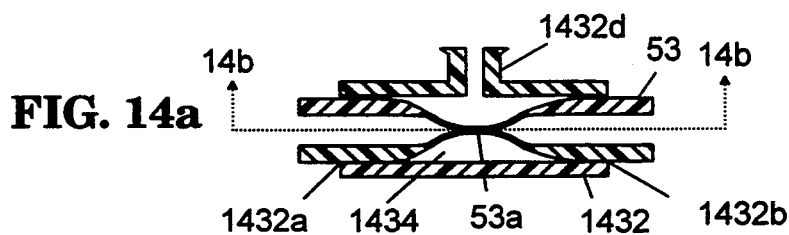
FIG. 14(a) is a sectional view of another presently preferred embodiment of the pressure sensitive valve 531 similar to that illustrated in FIG. 2 with an elliptical midportion.
Figure 14B:
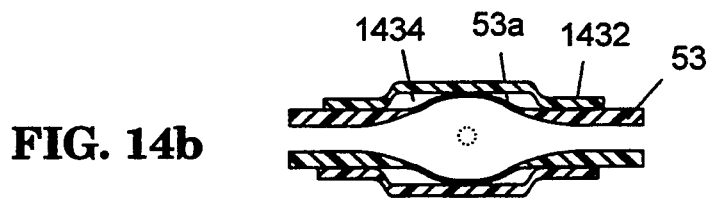
FIG. 14(b) is another sectional view of the pressure sensitive valve illustrated in FIG. 14(a)

Referring to FIG. 14(a) and 14(b) another presently preferred embodiment of the pressure sensitive valve 531 similar to that illustrated in FIG. 2 except that unitary tubing member 53 is sealed in enclosure 1432 which is cylindrical at its end but elliptical at the portion that overlays region 53a, said elliptical cross section allowing for accommodation of an enlarged diameter in one aspect of collapsed region 53a. For positive pressure application the housing's walls need to be somewhat inelastic but not necessarily rigid. For negative pressure applications, said wall needs to be sufficiently inelastic to withstand the expected negative pressure to be controlled. Housing 1432 may also be made by blow molding an inelastic material such as polycarbonate, polyvinylchloride, polyethylene, or the like. Housing 1432 provides a chamber with a lower interluminal volume 1434 than cylindrical chamber 534, thus requiring lower volume pressure regulators which translates to smaller, more sensitive and less expensive units.

Figure 8:
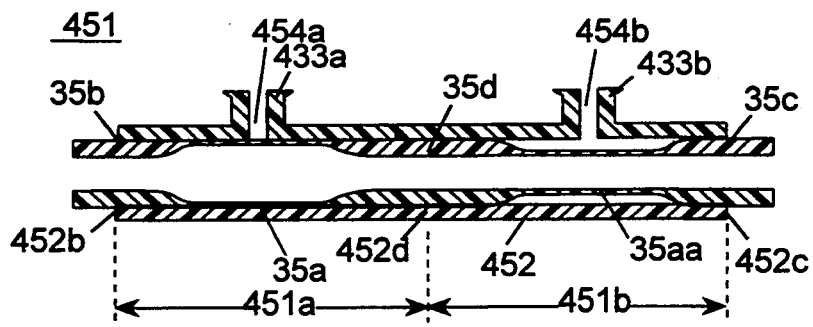
FIG. 8 is a sectional view of an alternate embodiment of valve 531 taken between lines 12 and 12' of FIG. 1 and illustrating a double cavity configuration wherein a pressure isolator is associated with a pressure sensitive valve at the inlet end thereof.

FIG. 8 illustrates a combination valve that incorporates two pressure sensitive valves. The first, at section 451a, is formed with thin wall section 35a serving as an inline pressure isolator as previously described in FIG. 25. The second, at section 451b, is formed with thin wall section 35aa serving as a pressure relief valve as described in FIG. 2. Both valves are incorporated into one housing embodiment 452 and made from one unitary tubing member 35. The two valves are independent of one another by way of a seal formed between housing 452 and unitary tubing 35 at 452d and 35d respectively, using the sealing techniques mentioned earlier for construction of valve 531 illustrated in FIG. 2. Pressure isolator 451a at the inlet, allows pressure measurement at the inlet to the pressure relief valve. Alternately, interluminal space 454a of the isolator valve 451a is connected via port 433a to pressure regulator 930, illustrated in FIG. 9. For example, isolator valve 451a may have a significant volume in the intraluminal space 35a relative to the volume of the elastic balloon of the pressure regulator 930, which is pressurized to a fixed pressure. Should the inlet pressure in unitary tubing 35 exceed the fixed pressure, the isolator valve would expand into the interluminal volume 454a thereby expanding the volume of the elastic balloon 933, which would indicate that the pressure in the unitary tubing has exceeded the fixed pressure. This can be verified, or also directly indicated by use of a clear housing 452. When the open expanded thin wall section 35a of the first pressure sensitive valve contacts the walls of the housing 452, the optical characteristics of housing 452 change, indicating that a predetermined pressure has been exceeded. Alternately port 433a may be connected to a standard electronic pressure transducer (such as that made by American Edwards) or other pressure indicators such as pressure gauges. Changes in the blood pressure would be transferred across the wall of 35a and transmitted to the pressure indicators. For a damped signal, air can be used as the transmitting fluid. For higher fidelity, water or a physiological solution, such as normal saline, can be the transmitting fluid. The use of a sterile physiological solution has the added advantage that it provides an acceptable environment to blood should the thin wall of the pressure sensitive valve develop a leak.

Other combinations of valves can be made wherein the combination valves can house more than two functional regions. For example, a combination valve can house a valve similar to 531, 571 and a pressure isolator 451a.

Figure 26:
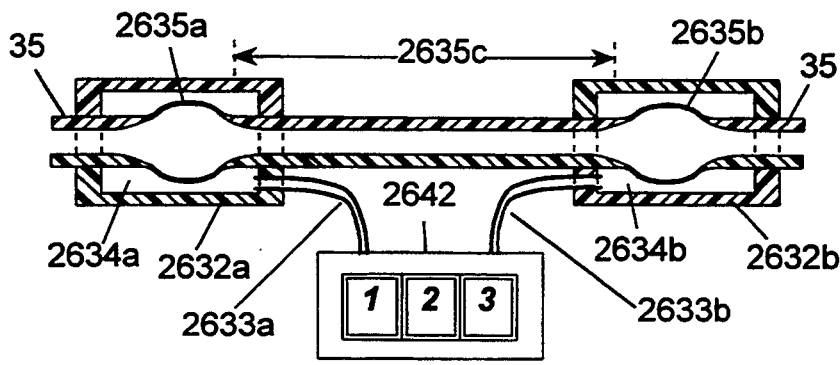
FIG. 26 illustrates how one unitary tube incorporating two independent pressure isolation valves separated by a tubing section with a known resistance to flow, can serve to determine flow.

Another combination would utilize two pressure isolation valves incorporated within one unitary tube, similar to that shown in FIG. 8, and with section 35d providing a known resistance to flow. By measuring the pressure difference between port 433a and port 433b, and knowing the resistance characteristics of section 35d, flow can be calculated. Thus, two pressure isolation valves and a resistance therebetween can be used to measure flow. An alternate design is illustrated in FIG. 26.

Valve 281 when placed in unitary tubing 28 between the patient and suction pump 9, functions to prevent excess suction from being applied to the patient. This is achieved by having the thin walled section 53a of the valve described in FIG. 7 precollapsed in the closed position as illustrated in FIG. 5 as its natural state. Outlet 533 is connected to a pressure regulator 1131 or 1230, as will be described hereinafter in FIGS. 11 or 12 and 13 respectively, that regulate the negative pressure applied to the interluminal chamber 534 of FIG. 7. Valve 281 then functions as follows: initially the valve is closed, a vacuum, set by the user, is applied to chamber 534 by a vacuum regulator such as 1230 of FIG. 13, thereby expanding the walls of region 53a and opening the valve. Suction pump 9 is started and withdraws blood from the chest cavity (not shown). Should the user attempt to withdraw more blood than is available and the tip of the suction catheter (not shown) positioned in the chest cavity becomes obstructed by sucking against the chest wall, the negative pressure in the lumen of unitary tubing 53a would increase beyond the vacuum set by regulator 1230 of FIG. 13, thereby causing the thin wall of section 53a to collapse and close the valve. This isolates the patient from the excess suction generated by pump 9. Should the negative pressure between valve 281 and the patient subside and reach a lower negative pressure than that provided by pressure regulator 1230 of FIG. 13, the valve would reopen and blood withdrawal would continue.

The present invention can also be used to provide adjustable resistance to flow. When valve 231, illustrated in FIG. 1, is placed in unitary tubing 23 between the patient and venous reservoir 3, it functions to control the resistance to blood flow in the venous line, a useful function that facilitates the coming off, going on, or conduct of partial cardiopulmonary bypass. Resistance is controlled with a pressure sensitive valve similar to valve 531 illustrated in FIG. 2 for which the interluminal space of chamber 534 is controlled with a syringe 1910 illustrated in FIG. 19 connected to 534 via a standard tube. If a liquid, such as normal saline, is used as the fluid in syringe chamber 1934, valve chamber 534 and the interconnecting tubing then the volume of the interluminal space, may be controlled by syringe 1910. By infusing additional saline from the syringe into the valve, the interluminal space expands, causing a collapse of section 53a and a corresponding increase in resistance to flow. Similarly, withdrawal of saline decreases the interluminal space and causes a decrease in resistance to flow. Thus, it is possible to have the syringe precalibrated to indicate the relative cross sectional area of 53a that is open and therefore the relative resistance of the valve. This can be calculated from the volume of chamber 534 when the valve is fully open less the volume of 534 when the valve is fully closed. A calibration curve of volume vs. "openness" can be made and used for future valves with a syringe that is marked according to % cross sectional area for a particular valve as illustrated by indications 1938 illustrated in FIG. 19. The precalibrated syringe can also incorporate an adjusted locking piston (e.g. "Vari-Stop" Sherwood Medical Inc. St. Louis, Mo.).

As discussed before, the flutter of a volume sensitive valve used to adjust resistance to flow should be minimized. This can be achieved by increasing the wall thickness and/or hardness of section 53a.

FIG. 9 is a sectional view of one preferred embodiment of a pressure regulator consisting of a circular plastic basemember 932 configured to accept one open end of an elastic spherical balloon 933 held to, and sealed to, basemember 932 by compression fitting 932a that accepts a locking circular ring 935. The balloon 934 is sealed at its other open end 933b with check valve 936. Check valve 936 permits pressurization of chamber 934 which is formed by the balloon, the plastic basemember and the check valve. The pressure in chamber 934 is transmitted through opening 932b and through valve 101 in FIG. 10, through duct 533 to chamber 534 of pressure sensitive valve 531 in FIG. 2. The pressure-volume relationship of chamber 934 is determined by the elastic properties and physical dimensions of the balloon forming part of the chamber enclosure, as described in my co-pending application U.S. Ser. No. 267,235. The balloon provides a steady pressure over a range of volumes that is greater than the volume change required to open and close pressure sensitive valve 531. Check valve 936 can be, for example, Luer Style Syringe Check Valve Model #810ACS made by Halkey Medical of St. Petersburg, Fla. 33702-1098, whose open end accepts the luer fitting of a syringe and is designed to fill, hold and release controlled amount of fluids on demand.

Figure 18:
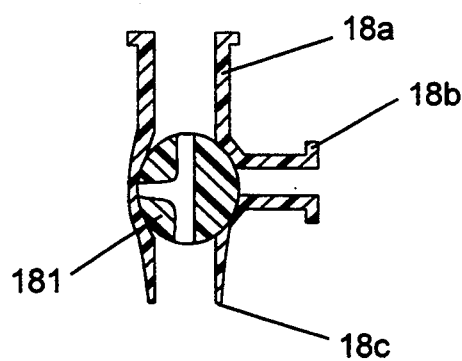
FIG. 18 illustrates a sectional view of a three way stopcock adapted for use with the present invention.

Alternatively, valve 936 can be replaced with a fitting that accepts a standard 3 port stopcock illustrated in FIG. 18. One port of the stopcock attaches to the balloon, another allowing changes in the balloon volume, and the third connected to a conduit leading to a pressure transducer. This arrangement allows precise measurements of the controlling pressures.

Figure 11:
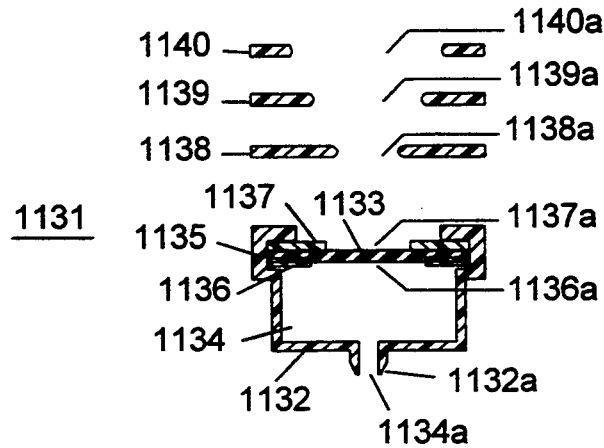
FIG. 11 is a sectional view of another preferred embodiment of a pressure regulator similar to FIG. 9 but utilizing a flat elastic membrane.
Figure 19:
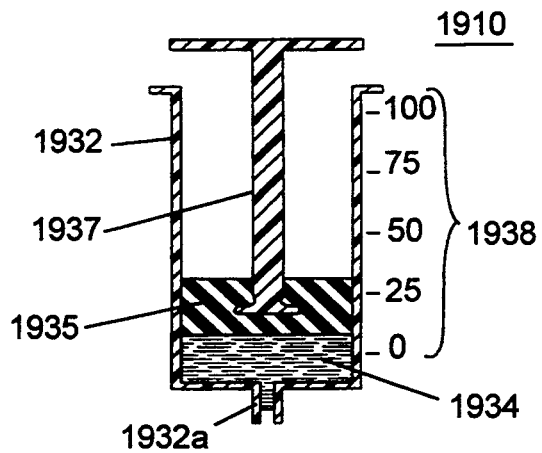
FIG. 19 illustrates a cross sectional view of a syringe calibrated to read the open area of a pressure sensitive valve.

FIG. 11 is a sectional view of another preferred embodiment of a pressure regulator similar to FIG. 9 but utilizing a flat elastic membrane 1133 to form one side of chamber 1134 of the pressure regulator. Diaphragm 1133 is supported by disk 1137 with inside diameter 1137a on its external side and by disk 1136 with inside diameter 1136a on its internal side. This design allows for the control of either pressure or suction by either pressurizing or evacuating chamber 1134 respectively. Positive pressure may be regulated or controlled by supporting rigid disk 1137 and negative pressure of the vacuum controlled by the inside diameter of rigid disk 1136, both of which can be independently changed. The absolute value of either pressure or vacuum depends on the thickness and the diameter of the free moving section, as determined by the supporting disk, of the elastic membrane disk, and the elastic properties of the specific membrane used. Disks 1136, 1137, 1138, 1139 and 1140 can be appropriately marked and easily interchanged by the manufacturer or end user as a simple and inexpensive method to provide large variations in pressure with the same diaphragm. Disk 1138, with the smallest opening, 1138a, provides the highest pressure and disk 1140, with the largest opening 1140a, provides the lowest pressure. The volume of chamber 1134 can be adjusted by various ways, as for example by use of a three way stopcock, shown in FIG. 18 with port 18a connected to port 1132a of regulator 1131, port 18c connected to port 533 of pressure sensitive valve 531 and port 18b attached to a syringe for volume adjustments. The syringe can be a standard syringe widely available to practitioners in the field, or a precalibrated syringe as illustrated in FIG. 19. The three way stopcock can be eliminated by using a syringe that has a locking piston (e.g. "Vari-Stop" Sherwood Medical Inc. St. Louis, Mo.). It should be understood that the syringe provides means for charging the mass of the controlling fluid in the interluminal space as well as in chamber 1134. Increase or decrease in mass introduced by the syringe provides an increase or decrease in pressure and/or volume respectively.

Figure 12:
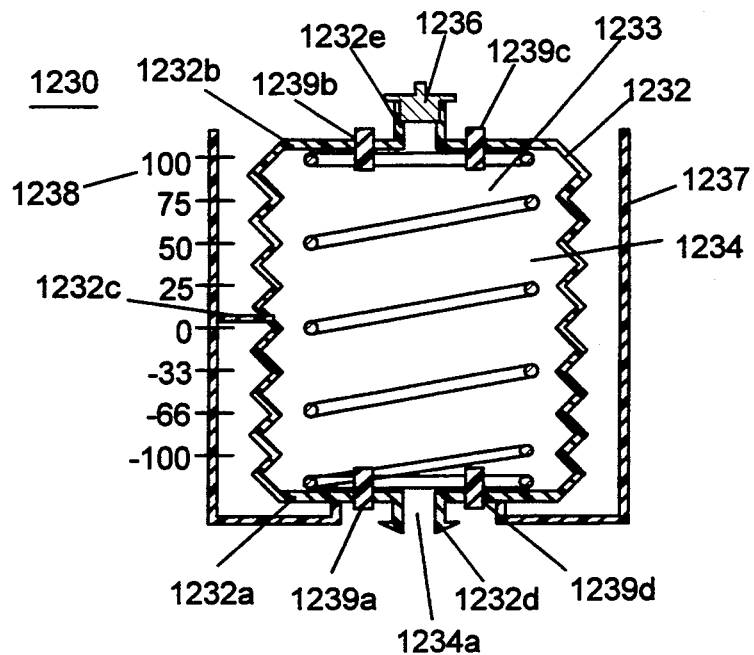
FIG. 12 is a sectional view of another preferred embodiment of a pressure regulator similar to FIG. 11 but utilizing a spring, sealed in a flexible polymeric envelope incorporating a pressure indicator.

FIG. 12 is a sectional view of another preferred embodiment of a pressure regulator similar to FIG. 11 except that spring 1233 replaces the elastic force of diaphragm 1133 in FIG. 11. The spring is housed in, and attached to, flexible polymeric envelope 1232 forming chamber 1234. The connections are made at 1232a with 1239a and 1239d and at 1232b with 1239b and 1239c. The combination of the spring for elasticity and the envelope for sealing can provide adjustments for either control of pressure by expanding the spring, or of suction by compressing the spring via the addition or subtraction of volume into chamber 1234 respectively. This volume may be altered via check valve 1236 sealed in port 1232e, in a manner similar to that described previously for pressure regulator 930 in FIG. 9. The controlled negative or positive pressure is conducted through orifice 1234a, an interconnecting tubing (not shown) to port 533 of valve 531 and thereby to chamber 534, to impart selected negative or positive pressure upon section 53a of valve 531. Unlike the elastic material used with pressure regulator 930 and 1131 the pressure generated by spring 1233 is very dependent on the degree of compression of the spring and therefore on the volume within chamber 1234. This can be used to the user's advantage by providing scale 1238 and pointer 1232c, the combination of which indicate the degree of negative or positive pressure applied on section 53a. Pressure scale 1238 can be expressed as a % of maximum negative or positive pressure possible, in mm Hg or alternatively in cm of $H_2O$.

The ratio of the volume 1234 of regulator 1230 relative to the volume change in 53a required to open a closed valve can be used to provide a variable suction regulator. If said change in volume of 53a is large compared to volume 1234 then as the valve closes volume 1234 must decrease thereby compressing spring 1233 and generating greater suction on thin wall section 53a. If the change in volume 53a is very small compared to the volume 1234 then there will be no significant change in 1234 as the valve opens or closes and the suction applied to 53a would be essentially unchanged. It is possible to add another volume between pressure controller 1230 and controlled valve 531 thereby having a choice of the type of suction regulation, steady or variable. The added volume can be in the form of a tube of various lengths or calibrated syringe 1910 of FIG. 19 connected to valve 1236. With syringe 1910, volume 1234 would be connected to volume 1934 through port 1932a and the total volume of 1234 plus volume 1934 would be adjusted by moving plunger 1935 along scale 1938. This syringe incorporates a mechanism (not shown) to lock the plunger in its desired position as previously described.

The ratio of the volume 1234 of regulator 1230 relative to the volume change in 53a required to open a closed valve can also be used to provide a variable pressure regulator. If the said change in volume of 53a is large compared to volume 1234 then as the valve opens volume 1234 must increase thereby expanding spring 1233 and generating greater pressure on thin wall section 53a. If the change in said volume 53a is very small compared to the volume 1234 then there will be no significant change in 1234 as the valve opens or closes and the pressure applied to 53a would be essentially unchanged. The type of pressure regulation, steady or variable is determined by the user who can, as described for the aforementioned suction regulator, add another volume between pressure controller 1230 and controlled valve 531.

Figure 13:
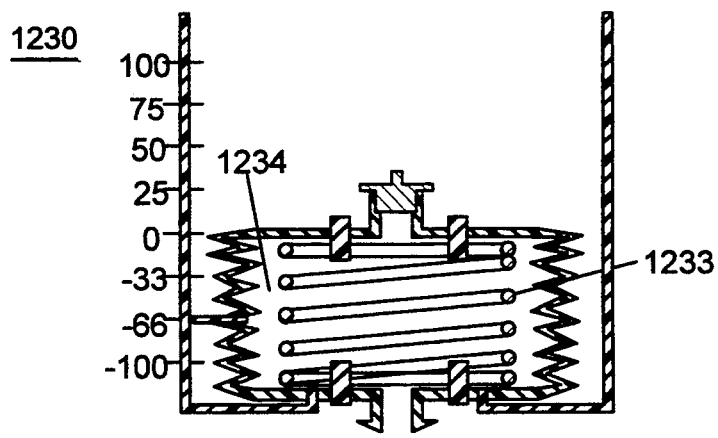
FIG. 13 is a sectional view of another preferred embodiment of a pressure regulator similar to FIG. 12 but with the spring illustrated in the compressed mode.

FIG. 13 illustrates a sectional view of a negative pressure regulator 1230 illustrated in FIG. 12 with spring 1233, shown in the compressed mode, used to apply a controlled negative pressure (suction). The compression was produced by decreasing volume 1234 via an adjustable syringe.

FIG. 15 illustrates cylindrical balloon 1533 used in place of spherical balloon 933 in FIG. 9 closed at one end with valve 936 and connected directly to port 532d of valve 531. Check valve 936 is being used as described in FIG. 9, and said cylindrical balloon serving an identical purpose as the spherical balloon 933 in FIG. 9. The cylindrical balloon has the advantage of low manufacturing costs, since it may be formed by extrusion rather than molding or dipping as is the case with a spherical balloon. The cylindrical balloon can also be made to have an internal diameter that would accept a standard check valve as for example Luer Style Syringe Check Valve Model #810ACS made by Halkey Medical which requires an opening of 0.300". The pressure-volume relationship of the cylindrical balloon is determined by the elastic properties and physical dimensions of the balloon forming part of the chamber enclosure, as described in co-pending application U.S. Pat. No. 267,235. The pressure required to inflate a cylindrical balloon is a function of its internal diameter. For short balloons for the ratio of ID/length <10, the length also affects the inflating pressure. For such balloons an effective diameter can approximate the diameter to be used in the relationship between diameter and inflating pressure. Since the effective diameter for a short cylinder can be approximated by (Length×Diameter)/-(Length+Diameter), then the inflating pressure for any specific cylindrical balloon can be adjusted by adjusting the length of the balloon that is allowed to expand. To that end, cylindrical sleeve 1535 placed over balloon 1533 limits the balloon expansion which results in a smaller effective diameter and therefore a higher inflating pressure. Sleeve 1535 can also provide mechanical support to prevent the elastic cylinder from disconnecting at 1533b from port 532d of valve 531. Sleeve 1535 can be replaced by other sleeves of different lengths, as for example sleeves 1536 or 1537, to yield different pressure, each of said sleeves can be marked appropriately to indicate the pressure it provides. It is also possible to provide different pressure vs. volume curves by having the sleeve made of an elastic material, the combination of the balloon and sleeve adapted to give desired results. It also should be obvious from the information given that the cylindrical balloon 1533 can be connected to port 532d via a plastic cap similar to 932b shown in FIG. 9. The cylindrical balloon can for example be made from extruded latex tubing with an ID of 0.250", a wall thickness of 0.025" and cut to a length of 1.0 to 2.0".

FIG. 16 illustrates another preferred embodiment of the pressure sensitive valve 531 similar to that illustrated in FIG. 14(a) except that housing 1632 incorporates pressure regulator enclosure 1632e. The pressure regulator of device 1630 is identical to that previously described for FIG. 11, except for the addition of port 1632g that accepts check valve 936. Chamber 1634b is sealed by elastic diaphragm 1133 at one end and connected through passage 1634c to interluminal space 1634a at its other end. Port 1632g is sealed with check valve 936 which is used to adjust negative or positive pressure of chambers 1634a. Interconnecting passage 1634c, formed by circular wall 1632f, has a smaller diameter than the diameter required for diaphragm 1133, the smaller diameter prevents region 53a from accidentally herniating when the interluminal pressure 1634a is low and the blood pressure is high. The circular shape eliminates sharp edges. Embodiment 1630 can be made by blow molding of inelastic material such as polycarbonate, or of flexible thermoplastic, such as polyvinyl chloride, allowing said housing to seal the thin wall tubing 2271 to rigid connectors 2275 and 2276 illustrated in FIG. 22 as will be described hereinafter. Housing 1630 has the advantage of fewer parts and simpler assembly both of which reduce cost and increase reliability.

FIG. 17(a) is a sectional view of another preferred embodiment of a pressure regulator similar to that shown in FIG. 9 and FIG. 15 consisting of one open end of an elastic spherical or cylindrical balloon 933 sealed to port 532d of valve 531 in FIG. 2, for example, by compression fitting 937a. The other end of the balloon, 933b, is sealed with check valve 936. The pressure-volume relationship of chamber 934, determined by the elastic properties and physical dimensions of the balloon, described previously, is modified by conical housing 937 as follows: the wide base of the cone slips over balloon 933 via opening 937 at its base said opening also may serve to support balloon 933 seal to port 532d, for example. Initially, when the balloon is inflated, its walls are free to expand resulting in an unmodified normal pressure. Upon further inflation 933aa the balloon walls encounter the conical walls of the housing, the latter impeding expansion radially and forcing expansion laterally resulting in higher inflation pressure. Still further inflation 933bb encounters even smaller housing diameter thereby resulting in even higher inflation pressure. It should be obvious to those skilled in the art that the inflating pressure can be controlled by the ratio of the balloon diameter to the housing diameter and angle β describing the cone. This property can be used to form scale 938 along wall of cone to indicate the pressure corresponding to inflation pressure. To prevent air entrapment between the balloon walls and the housing wall, which can affect the inflating pressure, hole 937b in housing and/or the inside surface of said cone, is formed with grooves 937c illustrated in FIG. 17(b) the latter forming a continuum between any radial cross section of the cone and atmosphere.

FIG. 18 illustrates an example of a standard three way stopcock, which was described for example in FIG. 11.

It should be understood by those skilled in the art that valve 936 of pressure regulators 930, 1530, 1630, and 1730 as well as valve 1236 of pressure regulator 1230, can be replaced by a 3 way stopcock illustrated in FIG. 18 placed between corresponding orifices such as 932d of FIG. 17 and 1232d of FIG. 12 and orifice 533 of pressure sensitive valve 531. The 3-way stopcock has the advantage that one of its ports can be connected to a pressure transducer for more precise measurement of the controlling pressure. It should also be understood by those skilled in the art that all connections required to be made by the user would have an advantage if they are formed by standard luer-lock fitting such as 18a 18b and 18c illustrated for the stopcock illustrated in FIG. 18.

FIG. 19 illustrates a cross sectional view of a calibrated syringe with barrel 1932 and plunger 1937 connected to a sealing rubber piston 1935. A standard syringe is used, except that a scale that corresponds to the open area of valve 531 as previously described, as for example for valve 231, and hereinafter described, is imprinted on the barrel. In addition, the piston can be locked in any position, such as the aforementioned Vari-Stop made by Sherwood Medical. Such a syringe can be particularly useful for the previously described applications of adjusting the resistance of valve 231 described in FIG. 1, or the volume of the aforementioned pressure/vacuum regulator described in FIG. 12.

Figure 20:
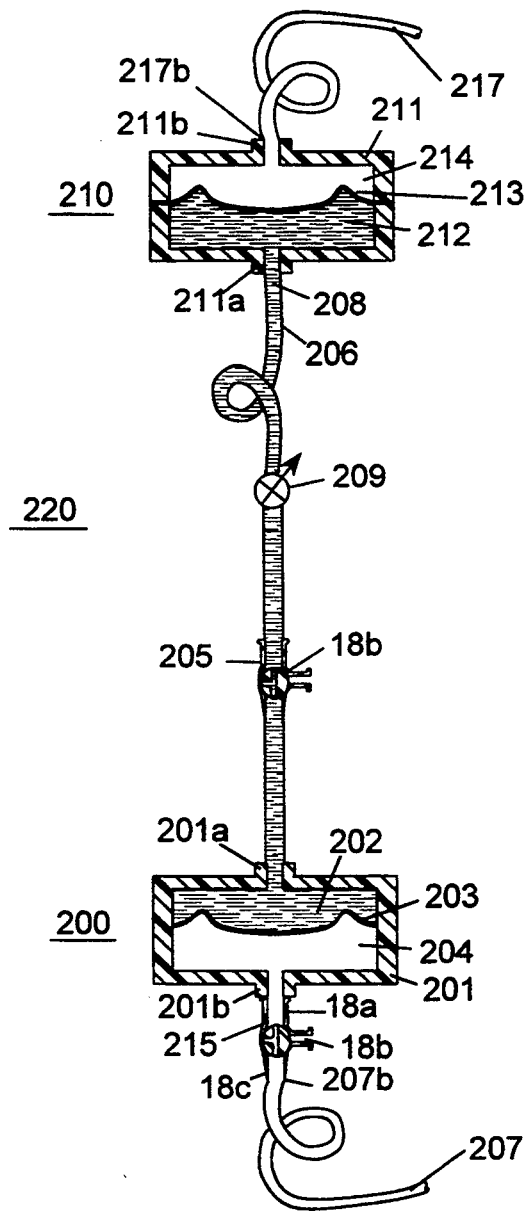
FIG. 20 illustrates a cross sectional view of an accurate pressure or vacuum regulator.

FIG. 20 illustrates a cross sectional view of a device that can be used to regulate pressure or vacuum of a closed system that requires relatively small volume changes, in a simple but very accurate manner. The device is composed of two essentially identical pressure isolators 200 and 210 interconnected via flexible tube 206 and three way stopcock 205. Pressure isolator 200 is composed of rigid, generally cylindrical, transparent, housing 201. Housing 201 encompasses two variable volume chambers 202 and 204 with a common wall made of loose diaphragm 203 circumferentially sealed midway in housing 201. The position of the freely moving diaphragm determines the relative volume of chambers 202 and 204. The volume of either chamber 202 or 204 can be anywhere from almost 0 to almost the volume formed by housing 201, and can be expressed as follows: volume 202 + volume 204 = the volume formed by housing 201 less the volume of diaphragm 203. Diaphragm 203 can move freely with inconsequential elastic stress or force, until it is supported by the walls of housing 201. Pressure isolator 210 is similar in construction and function to pressure isolator 200. It too is composed of rigid, generally cylindrical, housing 211 forming a chamber that is divided into two variable volume chambers 212 and 214 with a common wall made of loose diaphragm 213 circumfrentially sealed midway in housing 211. Pressure isolators 200 and 210 can be similar in construction to the Pressure Monitor Separator (Cat. No. PMS-2) made by Delta Medical Industries Costa Mesa Calif. 92626.

To form a pressure regulator, chamber 202 of pressure isolator 200 is connected to chamber 212 of pressure isolator 200 via tube 206, the connections made at port 201a and 211a respectively. The entire volume of chambers 202 and 212, the interconnecting tubing and stopcock 205 is filled with liquid 208. During said filling it is advantageous, but not essential, to having diaphragms 203 and 213 at their midposition (e.g. volume 202 = volume 204 and volume 212 = volume 214). The filling may be made with 3-way stopcock 205 interposed between tubing and said chambers, said stopcock better illustrated in FIG. 18 and connections made for example via standard luer-lock connectors. Thus, chambers 202 and 212 are interconnected and filled with a liquid, the liquid being able to flow freely therebetween. The direction of flow depends on the pressure difference between diaphragms 203 and 213, this difference equaling the hydraulic height plus the pressure difference between chambers 204 and 214.

Figure 21:
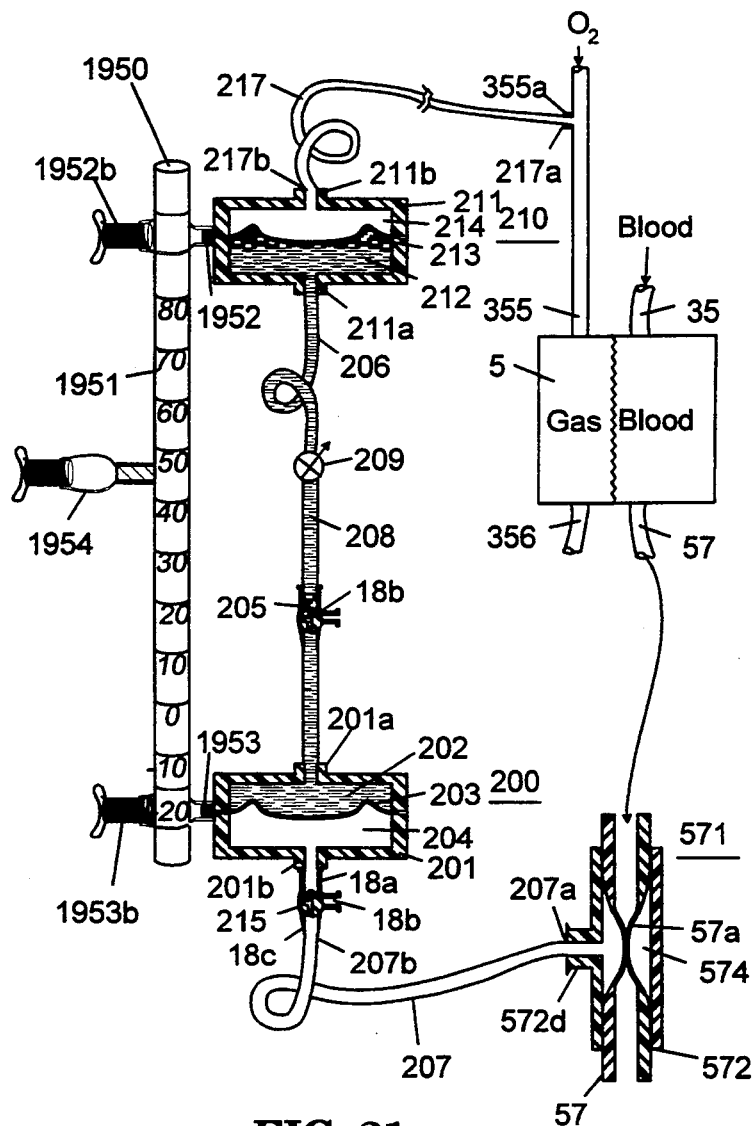
FIG. 21 illustrates a pressure regulator described in FIG. 20 combined with a pressure relief valve to assure that the pressure on the blood side of a microporous oxygenator is always greater than the pressure on the gas side of the oxygenator.

FIG. 21 illustrates pressure regulation with pressure regulator 210. Here, chamber 204 of pressure isolator 200 is connected, for example, to interluminal volume 574 of pressure sensitive valve 571 via stopcock 215, tube 207, and fitting 207a engaging port 572d. It can be advantageous to have said connections made via standard luer-lock fittings, tight slip-on connection, or through permanent connections that would reduce the chances of fluid 208 leaking. Pressure isolator 210 is elevated above pressure isolator 200 to a height that will give a hydraulic pressure equal to the control pressure desired for pressure relief valve 571. For example, this can be done by moving clamp 1952 vertically with respect to clamp 1953, along support rod 1950 said clamps supporting pressure isolators 210 and 200 respectively. Locking mechanisms 1952b and 1953b can be opened to slide clamps 1952 and 1953 respectively, and closed at the desired height. To facilitate determination of height differences between pressure isolator 210 and 200 scale 1951 can be incorporated into rod 1950. Using stopcock 215 and a syringe, the sealed volume formed by the chambers 574 and 204 and tube 218 is pressurized with a fluid, for example air, until diaphragm 213 is above its midpoint. This assure that the diaphragm can move freely without being impeded by housing 201 and pressure is controlled over the expected changes in volume 574 due to the valve opening and closing. Negative pressure can be controlled by either lowering pressure isolator 210 below pressure isolator 200, or by engaging port 572d of valve 571 with tube 217 instead of tube 207. The aforementioned regulation requires that the volume change due to movement of said diaphragm be greater than the volume change in chamber 574 due to region 57a intended opening and closing. In addition, the volume change in 204 and 202 should not cause a significant change in overall hydraulic pressure. This can be achieved by enlarging the cross sectional area of chambers 202 and 204 to provide said chamber with a volume that is significantly above the volume change required to affect the opening/closing of controlled pressure valve. To further minimize the changes in regulated pressure due to diaphragm motion, it is advantageous to make isolators 200 and 210 identical in all respects and provide a linear change in volume due to a vertical motion of the diaphragms. This design would allow liquid 208 moving vertically to cause a change in volume of chambers 202 and 212 without changing the controlled pressure. For example, a decrease in volume of chamber 212 is accompanied by a drop in the liquid level relative to scale 1951. However, the decrease in volume of chamber 202 is also accompanied by an increase in volume 212 of chamber 212 which in turn is accompanied by a drop in its liquid along scale 1951 said drop equaling the aforementioned drop in chamber 200. Since the two levels move equal vertical distance, there is no net change in the pressure liquid 208 generates. It should be pointed out that tubes 206 and 207 allow pressure isolator 200 to be placed at a variety of heights relative to valve 571 providing large possible changes of positive or negative pressure control. Liquid 208 is chosen according to the pressure or vacuum desired, using liquids with low density (e.g. saline) for low pressure and liquids with high density (e.g. mercury) for high pressure. The limiting factor being accuracy, the greater the height difference between ports 211a and 201a as compared to the liquid levels in chambers 202 and 212 the greater the accuracy. The accuracy can also be increased by using a flexible but inelastic tube 206 so as to prevent any changes in the liquid level due to tube 206 herniating. If high density (e.g. mercury) is used for liquid 208 then, if desired, it is possible to change the fluid in chambers 204, 574 and tubing 207 from gas to low density liquid (e.g. saline) without causing a significant error in controlled pressure. The regulated pressure set initially is also maintained by rod 1950 and locking clamps 1952 and 1953 that fix the distance between pressure isolators 200 and 210.

By utilizing liquid in tubing 207, pressure regulator 210 can also be used to facilitate control over fluttering of pressure relief valve being controlled, as described before. Valve fluttering can also be controlled by placing adjustable valve 209 in tube 206 or properly choosing the internal diameter of tube 206. Port 211b can be either connected to a pressure or vacuum source or be left open to atmosphere. Housings 201 and 211 can be made of rigid thermoplastic such as polyvinyl chloride and diaphragm 203 can be a rolling diaphragm that provides inconsequential resistance to movement of said diaphragm.

FIG. 21 also illustrates how the pressure regulator, described in FIG. 20, in combination with pressure relief valve identical to valve 531, as illustrated in FIG. 2, can be used to assure that the pressure on the blood side of a microporous oxygenator is always greater than the pressure on the gas side of the oxygenator. For this purpose valve 571, shown in FIG. 1 and which is identical to valve 531, is inserted at the outlet of membrane oxygenator 5 in tube 57. Chamber 204 of pressure isolator 200 is connected to chamber 574 via port 572d of valve 571. Pressure isolator 210 is raised above pressure isolator 200 to impart sufficient pressure on region 57a of valve 571 to insure its closure. Tube 217 interconnects chamber 214 of isolator 210 via a port 355a to tube 355 the latter supplying gas to oxygenator 5. This interconnection assures that the pressure in chamber 214 is equal to the inlet gas pressure, said gas pressure being transmitted through diaphragm 213, liquid 208, diaphragm 203, and fluid 218 to chamber 574 and applied to thin walled section 57a of valve 571. Thus, the pressure applied on section 57a is equal to the inlet gas pressure plus the hydraulic pressure regulated by device 220. Valve 571 remains closed unless the blood pressure in tube 57 overcomes the combined aforementioned pressures. Should the gas pressure at the inlet to the oxygenator increase, the valve will close until the backed up blood flow builds the additional pressure in tube 57 to overcome the additional pressure on the gas side.

Figure 22:
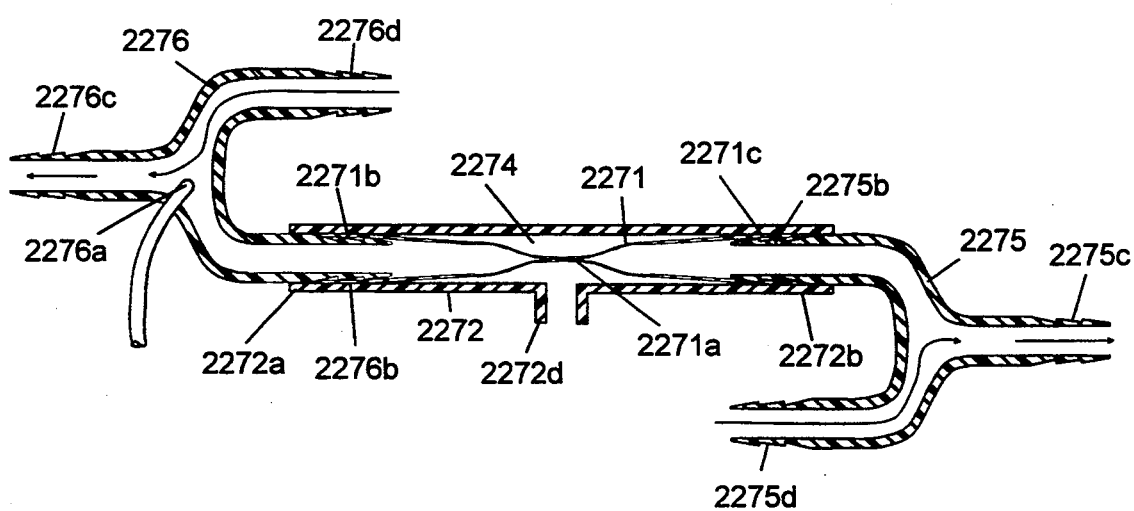
FIG. 22 illustrates a pressure relief valve utilizing rigid 'Y-connectors' for valve assembly and blood flow and a flexible housing to seal the thin wall sleeve to said 'Y-connectors'.

FIG. 22 illustrates a cross sectional view of a pressure relief valve utilizing 'Y-connectors', thin wall tube and elastic housing for pressure sensitive valve assembly and blood flow control. Thin wall tube 2271 with one end affixed to Y-connector 2276 at 2276b and the other end affixed to Y-connector 2275 at 2275b, forms a smooth blood path. End 2275c and end 2275d of said Y-connector 2275 are connected to venous reservoir 3 and venous line 23 respectively as shown in FIG. 1. End 2276c and end 2276d of said Y-connector 2276 are connected to arterial line leading to patient 2 and to line 57 from oxygenator 5 shown respectively in FIG. 1. The Y-connectors used, can be for example, be standard connectors supplied by Texas Medical Products of Houston Texas. Housing 2272 seals thin wall tube 2271 by forming a tight fit over 2271b onto 2276b at end 2272a and a tight fit over 2271c onto 2276b at end 2272b to form chamber 2274 whose pressure, positive or negative, can be adjusted as described previously. Thin wall tube 2271 can be made of a thermoplastic, as for example polyurethane or polyvinyl chloride, as described previously, and its section 2271a serving as the pressure sensitive section can be formed as described in FIGS. 4, 5 and 6. The advantages of this design are that the valve assembly requires no additional connectors, and it makes use of the already present Y-connectors that are used in the cardiopulmonary bypass circuit to form the recirculating line needed for priming. Similarly, this valve can also be used to bypass the arterial filter as valve 771 shown in FIG. 1. Pressure sensitive section 2271 can also be formed from a unitary tubing, as described in FIG. 14(a).

Figure 23:
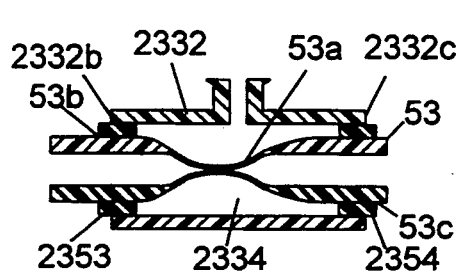
FIG. 23 illustrates an alternate embodiment forming an interluminal space for a pressure sensitive valve utilizing sleeves to seal between housing and unitary tubing.

FIG. 23 illustrates design utilizing a cylindrical spacers 2353 and 2354 serving to secure and seal the connection between housing 2332 and unitary tubing 53. Enclosed interluminal chamber 2334 is formed by sealing sleeve 2353 and 2354 to housing 2332 at ends 2332b and 2332c and the outer diameter of tube 53 at ends 53b and 53c respectively. The wall thickness of spacer 2354 can be large so as to enlarge volume 2334, as may be needed for a pressure isolator, or it may be thin to minimize volume 2334, as required for increased sensitivity of a pressure relief valve.

Figures 24A, 24B:
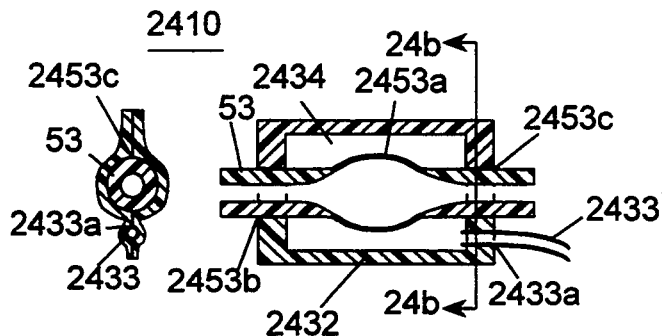
FIG. 24 illustrates an alternate embodiment forming an interluminal space for a pressure sensitive valve utilizing a thermoplastic cylindrical housing sleeve that is heat sealed to unitary tubing and pressure control line on each side of thin wall portion.

FIG. 24 illustrates an alternate embodiment forming an interluminal space 2434 for a pressure sensitive valve 2410 utilizing a thermoplastic cylindrical housing sleeve 2432. Sleeve 2432 is heat sealed to unitary tubing 53 at 2453b and 2453c and to pressure control line 2433 at 2433a, said seals hermetically enclosing thin walled section 2453a in formed space 2434. This design has the advantage that during assembly of the valve, it is easy to insert tube 53 into large cylindrical housing 2432 after which the seals are formed, which leads itself to mass automated production. In the previously described designs, assembly of unitary tubing 53 into a housing required tube 53 to tightly fit into housing ends.

FIG. 26 illustrates how two independent pressure isolation valves similar to that shown in FIG. 24, separated by tubing section 2635c with a known resistance to flow, all incorporated within one unitary tube can serve to determine flow. The pressure in section 2635a is transmitted via tube 2633a to pressure monitor 2642. Similarily, the pressure in section 2635b is also transmitted via tube 2633b to pressure monitor 2642. Pressure monitor 2642 may display each of the aforementioned pressures as well as their arithmetic difference. Using a precalibrated pressure drop vs. flow for section 2635c, flow can be calculated. This flow can be displayed directly by the pressure monitor.

I claim:

1. A noninvasive pressure monitoring system for pumps, said system comprising:
   (a) a length of tubing having at least one thin walled portion;
   (b) a pump having a drive means for pumping fluid through said tubing;
   (c) a pressure isolating chamber surrounding said thin walled portion said thin walled portion sealed within said chamber with said chamber having a monitoring port defined therein;
   (d) a fluid responsive transducer means connected to said pressure isolating chamber through said monitoring port, said transducer means connected to said drive means for controlling the speed of the pump when the pressure varies from a predetermined value.

2. A pressure monitoring system as claimed in claim 1 wherein the thin wall portion is on the inlet side of the pump and said pressure transducer is a low pressure transducer.

3. A pressure monitoring system as claimed in claim 2 wherein said pump is a roller pump.

4. A noninvasive pressure monitoring system for pumps as claimed in claim 3 wherein said tubing and said thin wall portion are formed of a single unitary length of polymeric tubing having a smooth fissureless inner wall.

5. A noninvasive pressure monitoring system for pumps as claimed in claim 2 wherein the inner diameter of said thin wall portion is greater than the inner diameter of said tubing.

6. A noninvasive pressure monitoring system for pumps as claimed in claim 2 wherein the inner diameter of said thin wall portion is less than the inner diameter of said tubing.

7. A pressure monitoring system as claim in claim 1 wherein the thin wall portion is on the outlet side of the pump and said pressure transducer is a high pressure transducer.

8. A pressure monitoring system as claimed in claim 7 wherein said pump is a roller pump.

9. A noninvasive pressure monitoring system for pumps as claimed in claim 8 wherein said tubing and said thin wall portion are formed of a single unitary length of polymeric tubing having a smooth fissureless inner wall.

10. A pressure monitoring system as claimed in claim 1 wherein said pump is a roller pump.

11. A noinvasive pressure monitoring system for pumps as claimed in claim 10, wherein said tubing and said thin wall portion are formed of a single unitary length of polymeric tubing having a smooth fissureless inner wall.

12. A pressure monitoring system as claimed in claim 1 wherein first and second thin wall portion are formed in said tubing with the first thin wall portion on the inlet side of the pump and the second thin wall portion on the outlet side of the pump, said system also including first and second pressure isolating chambers, with said first chamber surrounding said first thin wall portion and said second chamber surrounding said second thin wall portion, with a low pressure transducer connected to said first chamber and a high pressure transducer connected to said second chamber.

13. A noninvasive pressure monitoring system for pumps as claimed in claim 1 wherein the inner diameter of said thin wall portion is greater than the inner diameter of said tubing.

14. A noninvasive pressure monitoring system for pumps as claimed in claim 1 wherein the inner diameter of said thin wall portion is less than the inner diameter of said tubing.

15. A noninvasive pressure monitoring system for pumps as claimed in claim 1 wherein the inner diameter of said thin wall portion is the same as the inner diameter of said tubing.

16. A noninvasive pressure monitoring system for roller pumps, said system comprising:
 (a) a length of polymeric, unitary, fissureless tubing having first and second thin walled portions with a roller pump engaging section therebetween;
 (b) a roller pump having a drive means;
 (c) first and second pressure isolating chambers surrounding said first and second thin walled portions respectively, said first and second chambers having first and second respective monitoring ports defined therein;
 (d) a low pressure transducer connected to said first pressure isolating chamber through said first monitoring port, said transducer connected to said drive means for controlling the speed of the pump when the pressure drops below a predetermined value;
 (e) a high pressure transducer connected to said second pressure isolating chamber through said second monitoring port, said transducer connected to said drive means for controlling the speed of the pump when the pressure rises beyond a predetermined value.

17. A noninvasive pressure monitoring system for pumps as claimed in claim 1 wherein said tubing and said thin wall portion are formed of a single unitary length of polymeric tubing having a smooth fissureless inner wall.

18. A noninvasive pressure monitoring system for pumps as claimed in claim 16 wherein the inner diameter of said thin wall portions are greater than the inner diameter of said tubing.

19. A noninvasive pressure monitoring system for pumps as claimed in claim 16 wherein the inner diameter of said thin wall portions are less than the inner diameter of said tubing.

20. A noninvasive pressure monitoring system for controlling pump speed, said system comprising:
 (a) a length of tubing having first and second thin walled portions formed in said tubing;
 (b) a pump having a drive means for pumping fluid through said tubing, said pump engaging said tubing between said first thin walled portion and said second thin walled portion to define an inlet and outlet side of said pump;
 (c) a first and second pressure isolating chambers, with said first isolating chamber surrounding said first thin walled portion and said second isolating chamber surrounding said second thin walled portion;
 (d) a low pressure transducer connected to said first isolating chamber; and
 (e) a high pressure transducer connected to said second isolating chamber
 wherein said transducer means are connected to said drive means for controlling the speed of the pump when the pressure varies from a predetermined value.

* * * * *

UNITED STATES PATENT AND TRADEMARK OFFICE
CERTIFICATE OF CORRECTION

PATENT NO. : 5,336,051
DATED : August 9, 1994
INVENTOR(S) : Yehuda Tamari

It is certified that error appears in the above-indentified patent and that said Letters Patent is hereby corrected as shown below:

On title page, item [57] line 9: after "circuits" delete --,-- and insert --because--

Item [57] line 14: "so" should read --also--

Column 1, line 30: "controller" should read --controlled--

Column 1, line 31: "or" should read --of--

Column 1, line 54: "membranes" should read --membrane--

Column 1, line 67: "EMCO" should read --ECMO--

UNITED STATES PATENT AND TRADEMARK OFFICE
CERTIFICATE OF CORRECTION

PATENT NO.   : 5,336,051
DATED        : August 9, 1994
INVENTOR(S)  : Yehuda Tamari It is certified that error appears in the above-indentified patent and that said Letters Patent is hereby corrected as shown below:

Column 2, line 15:   "Lop"   should read --Loop--
    Column 2, line 23:   "Miss."  should read --MN--
    Column 2, line 26:   "pumps"  should read --pump--
    Column 2, line 35:   "method" should read --methods--
    Column 2, line 50:   "the"    should read --a--
    Column 2, lines 55 & 58: "wall" should read --walls--
    Column 2, line 60:   "weather" should read --whether--
    Column 2, line 62:   "pitch"  should read --pinch--
    Column 3, line 9:    "Rushnore" should read --Rushmore--

UNITED STATES PATENT AND TRADEMARK OFFICE
CERTIFICATE OF CORRECTION

PATENT NO. : 5,336,051
DATED : August 9, 1994
INVENTOR(S) : Yehuda Tamari

It is certified that error appears in the above-indentified patent and that said Letters Patent is hereby corrected as shown below:

Column 8, lines 1 & 2: "administrated" should read --administered--

Column 8, line 7: "the" should read --and--

Column 10, line 1: "Berniulli's" should read --Bernoulli's--

Column 16, line 8: "charging" should read --changing--

Column 18, line 42: after "inflation" insert --to--

Column 18, line 46: after "inflation" insert --to--

UNITED STATES PATENT AND TRADEMARK OFFICE
CERTIFICATE OF CORRECTION

PATENT NO. : 5,336,051
DATED : August 9, 1994
INVENTOR(S) : Yehuda Tamari

It is certified that error appears in the above-indentified patent and that said Letters Patent is hereby corrected as shown below:

Column 23, line 38, Claim 11: "noinvasive" should read --noninvasive--

Column 24, line 48, Claim 20: "of" should read --for--

Signed and Sealed this

Fourth Day of July, 1995

BRUCE LEHMAN

*Attest:*

*Attesting Officer*     *Commissioner of Patents and Trademarks*